United States Patent [19]
Brosius

[11] Patent Number: 5,829,974
[45] Date of Patent: Nov. 3, 1998

[54] ORTHODONTIC LIGATURE

[76] Inventor: David J. Brosius, 24603 Willowbrook Trail, Crete, Ill. 60417

[21] Appl. No.: 889,335

[22] Filed: Jul. 8, 1997

[51] Int. Cl.$^6$ ....................................................... A61C 3/00
[52] U.S. Cl. ................................................ 433/15; 433/11
[58] Field of Search ................................. 433/10, 11, 13, 433/15, 18

[56] References Cited

U.S. PATENT DOCUMENTS

| | | | |
|---|---|---|---|
| 2,767,469 | 10/1956 | Gladstone | 433/11 |
| 3,879,850 | 4/1975 | Wallshein | 433/18 |
| 4,950,158 | 8/1990 | Barngrover et al. | 433/11 |

OTHER PUBLICATIONS

Forestadent catalog 90/1, Bernhard Forster GmbH, pp. G6.8–G6.10, Jan. 1990.
Ormco catalog 070–0300 Rev. C, Ormco Corporation, p. 3, 1996.

*Primary Examiner*—John J. Wilson
*Attorney, Agent, or Firm*—Leydig, Voit & Mayer, Ltd.

[57] ABSTRACT

An improved orthodontic ligature for securing an arch wire to an orthodontic bracket has a stretchable ring member and an outwardly-extending grip extension integrally connected to the ring member. The ligature may be gripped at the grip extension using a pinching or clamping tool, facilitating installation of the ligature. An improved method of installing the ligature is also provided whereby the ring member is stretched to clear over tie wings of the bracket by pulling on the grip extension.

27 Claims, 2 Drawing Sheets

ORTHODONTIC LIGATURE

FIELD OF THE INVENTION

The present invention relates generally to orthodontic braces. More particularly, the present invention relates to elastic ligatures used for securing arch wires to orthodontic brackets.

BACKGROUND OF THE INVENTION

In general, orthodontic braces include a plurality of brackets, each being bonded to an individual tooth. A corrective force is applied to the brackets, and hence the teeth, by a shared arch wire. Each bracket has a central groove in which the arch wire is closely received, and the arch wire is typically retained in the groove by a binding element known in the art as a ligature or ligature tie. A ligature is typically an elastic band capable of being stretched around the bracket and biased across the arch wire.

To accommodate a ligature, a conventional bracket has at least one pair of oppositely-extending upper and lower tie wings extending away from the central arch wire groove. These tie wings serve to retain the ligature in an installed position--stretched around the bracket and across the arch wire groove. Accordingly, ligature installation involves stretching the ligature so as to loop around paired upper and lower tie wings, stretching from top to bottom around the bracket so as to securely bias the arch wire in the groove. Removal of a conventional ligature requires that the ligature be hooked or snagged in some manner and stretched back around the bracket tie wings.

A conventional ligature is a small elastic band with a uniform annular shape, as illustrated in FIGS. 1 and 1A. Installation is usually accomplished by gripping the ligature with a clamping or squeezing tool at some point on its circumference and stretching the ligature around tie wings on the bracket. Unfortunately, a conventional ligature provides a minimal amount of surface to grip during installation. As a result, the gripping tool is often extended too far across the central hole of the ligature, hindering installation. Conversely, sometimes the gripping tool engages too small of a section of the ligature, and the ligature may slip out of the tool's grip during attempted installation of the ligature, causing delay in the installation process and potentially causing discomfort to the patient. Thus, conventional ligatures can be awkward to manipulate, resulting in inconvenience to the orthodontist and discomfort to a patient.

It is desirable to provide a method of applying a ligature which minimizes the inconvenience and discomfort often associated with installation of conventional ligatures.

Therefore, a need exists for an orthodontic ligature which is more easily grippable, providing greater ease of installation, without sacrificing performance or aesthetic appearance.

SUMMARY OF THE INVENTION

It is an object of the present invention to provide an improved orthodontic ligature which is more easily gripped by a tool, in order to ease removal of the ligature from a carrier and installation of the ligature onto an orthodontic bracket.

To this end, the invention provides an improved ligature including an elastic ring member with a grip extension protruding therefrom. Preferably, the ligature is a unitary elastic element in which the ring member is generally annular. The grip extension is integrally connected to the ring member and extends radially away from the ring member. Installation of the ligature is accomplished by gripping it at the grip extension with a clamping or squeezing tool and using the tool to stretch the ligature around the wings on the bracket. In an installed position, the grip extension preferably lies adjacently behind or under a tie wing of the orthodontic bracket.

Accordingly, the present invention also provides a more efficient method for removing the improved ligature from a carrier and installing the ligature onto a conventional orthodontic bracket, which includes gripping the ligature at the grip extension and detaching it from a carrier, positioning the ring member of the ligature behind a tie wing, and pulling the grip extension to stretch the ring member. This method advantageously optimizes the stretching direction of the ring member and reduces the risk of inadvertently damaging or dislodging a bracket, or of causing patient injury or discomfort due to a loss of grip on the ligature.

The grip extension may be provided in various shapes and contours which optimize the grippability of the ligature when used with a particular bracket design or to be gripped by a particular tool.

The ligature is preferably shaped such that the ring member has a uniform cross-section substantially around the ligature. However, at the grip extension, the ligature has a cross-sectional area which is larger than that of the ring member. In other words, the protruding member is formed by a localized thickening of the ligature to a dimension greater than the dimension of the ring member. The annular thickness of the ligature at this grip member is at least 1.5 times, and preferably from about 2 to about 2.5 times the thickness of the ligature at the ring member at other annular positions.

An advantage of the present invention is that it provides an improved orthodontic ligature which is more easily gripped by a tool than is a conventional ligature. This advantage is attained without diminishing the aesthetic appearance of the completed braces.

Another advantage of the present invention is that it provides an improved method of applying an orthodontic ligature to a bracket. The improved method may be employed with less effort than the method conventionally used to apply a ligature to a bracket.

Yet another advantage of the present invention is that it provides a ligature which is more easily removed from a carrier, to which ligatures are usually attached when molded. Removal may be had by gripping the improved ligature at the extending grip portion and pulling it, to disconnect the ligature from the carrier.

Additional features and advantages of the present invention are described in, and will become apparent from, the detailed description of the preferred embodiments, the drawings, and the claims.

BRIEF DESCRIPTION OF THE DRAWINGS

For a more complete understanding of this invention reference should now be made to the embodiments illustrated in greater detail in the accompanying drawings and described below by way of examples of the invention.

In the drawings.

DETAILED DESCRIPTION OF THE PREFERRED EMBODIMENTS

Figure 1:
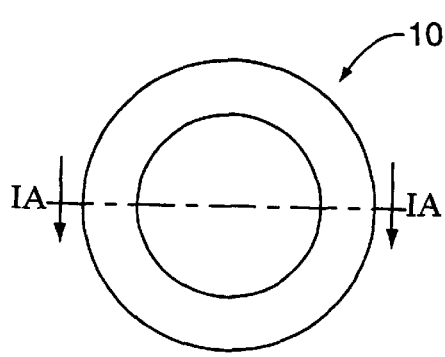
FIG. 1 is a plan view of a conventional ligature.
Figure 1A:
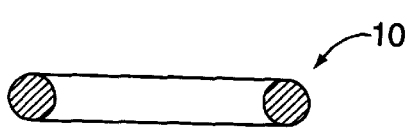
FIG. 1A is a sectional elevation view taken generally along line IA—IA of FIG. 1.

Referring now to the Figures, in which like numerals designate like parts, FIGS. 1 and 1A illustrate a conventional ligature 10. As shown in FIG. 1, the ligature 10 consists only of an annular body which, as shown in FIG. 1A, has a uniform circular cross-section. The size of the ligature 10 is small, having an outer diameter of about 0.110–0.125 inches. Due to the small size of its annular body, the conventional ligature 10 has proven to be difficult to grip by a pinching means. This is because the tool will usually grip either too much, in which case the tool blocks the central opening in the ligature, or too little, in which case the ligature slips from the tool when stretched. Ligatures in general have a high spring constant, and exert significant force when pulled. Thus installation of conventional ligatures is often difficult, inconvenient, and time-consuming.

Figure 2:
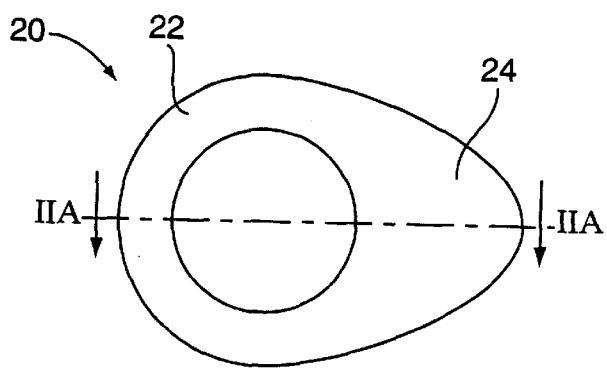
FIG. 2 is a plan view of a ligature according to an embodiment of the present invention.
Figure 2A:
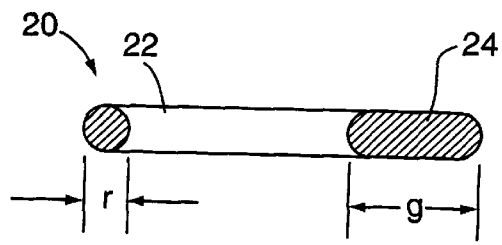
FIG. 2A is a sectional elevation taken generally along line IIA—IIA of FIG. 2.

Turning to FIGS. 2 and 2A, there is shown an orthodontic ligature 20 according to a preferred embodiment of the invention. The ligature 20 is preferably a unitary element molded from a high-strength elastomeric material of a conventional type suitable for orthodontic applications. The ligature 20 has a ring member 22 which has a uniformly circular shape and which is stretchably securable around an orthodontic bracket (discussed in greater detail below in connection with FIG. 3). The ring member 22 alone may be sized similarly to that of a conventional ligature 10 (FIG. 1), i.e., having an outer diameter of about 0.110–0.125 inches, and having an inner diameter corresponding to that of a similarly sized conventional ligature 10. As will be readily appreciated, the ligature 20 may also be made in other sizes as needed.

According to the invention, the ligature 20 further includes a grip extension 24 integrally connected to the ring member 22. The grip extension 24 protrudes away from the ring member 22, preferably in a radially outward direction, as shown. Around much of the circumference of the ligature 20, the ring 22 has a uniformly circular cross-sectional shape. More particularly, as illustrated in FIG. 2A, the ring 22 has a dimension in a radial direction referred to herein as a cross-sectional thickness r. At the grip member 24, however, the ligature 20 has a greater dimension in the radial direction, referred to herein as a cross-sectional thickness g. Preferably, the cross-sectional thickness g of the ligature 20 for the grip extension 24 is at least 1.5 times the cross-sectional thickness r of the ligature 20 for the ring member 22, and most preferably, the cross-sectional thickness g of the grip extension 24 is from about 2 to about 2.5 times the cross-sectional thickness r of the ring member 22.

Figure 3:
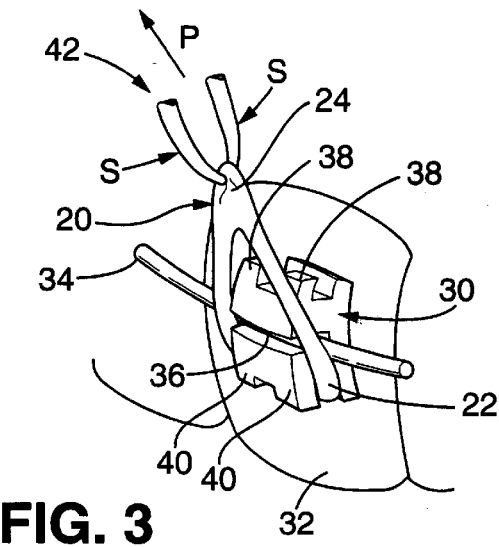
FIG. 3 is a perspective view of an orthodontic ligature according to the invention being stretchably manipulated with a tool onto an orthodontic bracket.

The grip extension 24 advantageously provides a convenient means by which the ligature 20 can be gripped for stretchable manipulation of the ring member 22. An exemplary application of the ligature 20 is illustrated in FIG. 3, wherein the improved ligature 20, subsequent to having been removed from a carrier (not shown), is shown being stretched around a standard orthodontic bracket 30. The bracket 30 is bonded to a tooth 32 in a conventional manner. An arch wire 34 extends transversely through a central arch wire groove 36 recessed into a front of the bracket 30. The standard bracket 30 has upper tie wings 38 and lower tie wings 40 which are oppositely-extending from each other and which extend away from the arch wire groove 36. In an installed or retaining position, the ring member 22 of the ligature 20 is looped around the bracket 30 so that it is held behind the tie wings 38, 40, and extends across the arch wire 34, securely biasing the arch wire into the groove 36.

According to the invention, the grip extension 24 of the ligature 20 is grippably engaged by a tool 42 adapted for effecting a pinching or clamping action, such as appropriate pliers, tweezers, or tongs. In FIG. 3, only the mated tips of the tool 42 are shown, with arrows S indicating a squeezing force applied from the tool 42 to the grip extension 24. When the grip extension 24 is gripped by the tool 42, the ligature 20 can be easily stretched. In particular, as FIG. 3 illustrates, the ring member 22 is held behind the lower tie wings 40, and a pulling force indicated by an arrow P causes a stretching of the ligature 20 so that the ring member 22 movably clears over the upper tie wings 38. According to a method of the invention, this gripping and pulling of the grip extension 24 is effective to stretchably install the ligature 20 onto the bracket by moving the ring member 22 to the location behind the tie wings 38.

Preferably, the ligature 20 is aligned so that the grip extension 24 ultimately resides generally behind the upper tie wings 38 or lower tie wings 40. Such an orientation facilitates an optimal stretching motion of the ring member 22 for clearing the tie wings, as illustrated in FIG. 3. The ligature 20 deforms during stretching, so that the grip extension 24 becomes substantially thinner and less predominant visually. Therefore, an advantage of the invention is that the grip extension 24 protrudes, if at all, only slightly from behind the tie wings 38 or 40 when the ligature is installed on the bracket 30. This allows the ligature to provide improved grip characteristics during installation without diminishing the appearance of the completed braces. Those skilled in the art will appreciate that the ligature according to the invention may also be used with other conventional styles of orthodontic brackets with tie wings other than the exemplary standard bracket 30 shown in FIG. 3.

Figure 4:
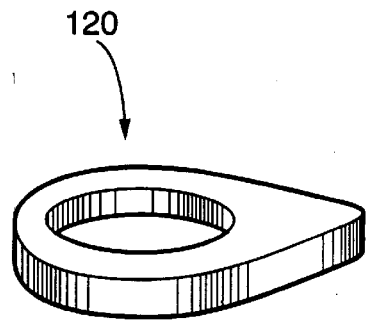
FIG. 4 is a perspective view of an alternative embodiment wherein the ligature has a generally rectangular cross-sectional shape.

FIG. 4 shows an alternative embodiment of a ligature 120 which is shaped to have a generally rectangular cross section.

Figure 5:
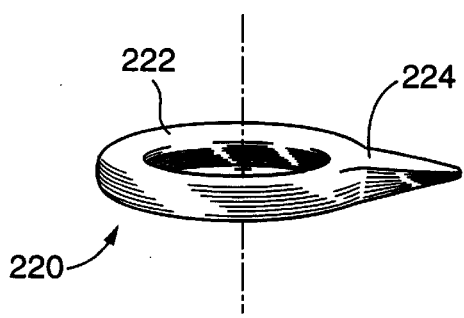
FIG. 5 is a perspective view of another embodiment of the invention, wherein the grip extension is generally triangular and tapered with a decreasing width in an outward direction.

Another alternative embodiment is shown in FIG. 5, in which a ligature 220 has a grip extension 224 that is shaped generally triangularly when viewed along a central axis of the ring member 222. Another possible feature of this embodiment of the grip extension 224 is that it has a tapered shape. Specifically, the ligature 220 has a width dimension which decreases outwardly along the grip extension 224.

Figure 6:
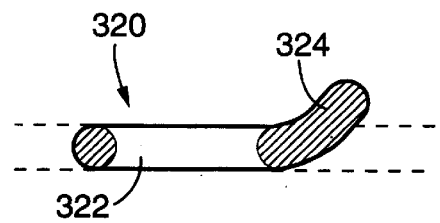
FIG. 6 is a sectional elevation of an alternative embodiment of the invention wherein the grip member extends non-radially out of a plane occupied by the ring member.

While the grip extension preferably protrudes radially outwardly relative to the ring member in the above-described embodiments, embodiments are possible wherein the grip extension protrudes also in a non-radial direction. For example, FIG. 6 illustrates a ligature 320 having a grip extension 324 which protrudes in a non-radial direction. Particularly, the grip extension 324 protrudes beyond a plane occupied by a ring member 322 of the ligature 320, the plane being generally indicated by dashed lines in FIG. 6. Because the ligatures according to the invention are necessarily flexed and twisted during use, the grip member can be aligned in a variety of directions relative to the ring member in an as-molded, or relaxed, position. Likewise, the ring member may alternatively be molded in a shape which deviates from the annular shape depicted in the FIGS., so long as it forms a loop which can be stretched around a bracket.

Figure 7:
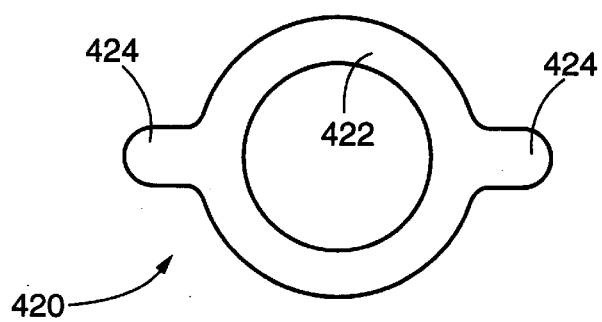
FIG. 7 is a plan view of an alternative embodiment of the invention having two grip extensions.

For providing grippability at multiple locations, a further alternative ligature 420 according to the invention as illustrated in FIG. 7 includes two cylindrically shaped grip extensions 424 integrally protruding from opposite sides of the ring member 422. Each of the grip extensions 424 is preferably aligned behind a respective upper or lower bracket tie wing when installed, to avoid detracting from the appearance of the completed braces.

While the invention is described herein in connection with certain preferred embodiments, there is no intent to limit it to those embodiments. On the contrary, it is recognized that various changes and modifications to the described embodiments will be apparent to those skilled in the art, particularly in view of the teachings herein, and that such changes and modifications may be made without departing from the spirit and scope of the present invention. For example, the grip extension of the ligature can be provided in numerous shapes other than those specifically illustrated. Such other exemplary grip-portion shapes include, but are not limited to, a shape which tapers in a widening manner away from the ring member, spheroidal, or a shape with a grip-enhancing contour such as an irregular surface, or a surface with one or more dimples or concave recesses. Also the grip extension could be configured with a hole disposed through it so that "gripping" is effected by extending a hooking tool through the hole. As an additional example, the relative dimensions of the improved ligature may be smaller or larger than indicated as needed. Accordingly, the appended claims are intended to cover all alternatives, equivalents, changes and modifications within the scope of the present invention.

What is claimed is:

1. An orthodontic ligature for securing an orthodontic arch wire to an orthodontic bracket, the ligature being unitarily formed on an elastomer and comprising: a generally annular ring member; and a grip extension connected to the ring member and extending away from the ring member, wherein said grip extension tapers in a decreasing manner away from said ring member.

2. The orthodontic ligature according to claim 1, wherein said grip extension extends radially outwardly from said ring member.

3. The orthodontic ligature according to claim 2, wherein said ligature has a first radial cross-sectional dimension for said ring member around most of a circumference of said ligature and a second radial cross-sectional dimension for said grip extension, wherein said second radial dimension is at least 1.5 times greater than the first radial cross-sectional dimension.

4. The orthodontic ligature according to claim 2, wherein said ligature has a first radial cross-sectional dimension for said ring member around most of a circumference of said ligature and a second radial cross-sectional dimension for said grip extension, wherein said second radial cross-sectional dimension is from about 2 to 2.5 times greater than said first radial cross-sectional dimension.

5. An orthodontic ligature for securing an orthodontic arch wire to an orthodontic bracket, the ligature being unitarily formed on an elastomer and comprising: a generally annular ring member; and a grip extension connected to the ring member and extending away from the ring member, wherein said grip extension has a generally triangular configuration as viewed along a central axis of the ring member.

6. The orthodontic ligature according to claim 5, wherein said grip extension extends radially outwardly from said ring member.

7. The orthodontic ligature according to claim 6, wherein said ligature has a first radial cross-sectional dimension for said ring member around most of a circumference of said ligature and a second radial cross-sectional dimension for said grip extension, wherein said second radial dimension is at least 1.5 times greater than the first radial cross-sectional dimension.

8. The orthodontic ligature according to claim 6, wherein said ligature has a first radial cross-sectional dimension for said ring member around most of a circumference of said ligature and a second radial cross-sectional dimension for said grip extension, wherein said second radial cross-sectional dimension is from about 2 to 2.5 times greater than said first radial cross-sectional dimension.

9. An orthodontic ligature for securing an orthodontic arch wire to an orthodontic bracket, the ligature being unitarily formed on an elastomer and comprising: a generally annular ring member; and a grip extension connected to the ring member and extending away from the ring member, wherein said grip extension is generally cylindrical.

10. The orthodontic ligature according to claim 9, wherein said grip extension extends radially outwardly from said ring member.

11. The orthodontic ligature according to claim 10, wherein said ligature has a first radial cross-sectional dimension for said ring member around most of a circumference of said ligature and a second radial cross-sectional dimension for said grip extension, wherein said second radial dimension is at least 1.5 times greater than the first radial cross-sectional dimension.

12. The orthodontic ligature according to claim 11, wherein said ligature has a first radial cross-sectional dimension for said ring member around most of a circumference of said ligature and a second radial cross-sectional dimension for said grip extension, wherein said second radial cross-sectional dimension is from about 2 to 2.5 times greater than said first radial cross-sectional dimension.

13. An elastic orthodontic ligature comprising: a ring member having a generally uniform first radial cross-sectional thickness; and at least a first grip extension protruding from said ring member; wherein the ligature has a second radial cross-sectional thickness at the grip extension which is greater than said first radial cross-sectional thickness, wherein said ligature has a width dimension extending perpendicularly to a plane defined by said ring member, wherein the width of the ligature decreases along the grip extension with increasing outward distance from the ring member.

14. The elastic orthodontic ligature according to claim 13, wherein said second cross-sectional thickness is from about 2 to 2.5 times the first radial cross-sectional thickness.

15. The elastic orthodontic ligature according to claim 13, wherein said grip extension is adapted for grippable engagement with a tool.

16. The elastic orthodontic ligature according to claim 13, further comprising a second protruding grip extension.

17. The elastic ligature according to claim 13, wherein said grip extension protrudes out of a plane in which the ring member generally resides.

18. An elastic orthodontic ligature comprising: a ring member having a generally uniform first radial cross-sectional thickness; and at least a first grip extension protruding from said ring member; wherein the ligature has a second radial cross-sectional thickness at the grip extension which is greater than said first radial cross-sectional thickness, wherein said grip extension is generally cylindrical.

19. The elastic orthodontic ligature according to claim 18, wherein said second cross-sectional thickness is from about 2 to 2.5 times the first radial cross-sectional thickness.

20. The elastic orthodontic ligature according to claim 18, wherein said grip extension is adapted for grippable engagement with a tool.

21. The elastic orthodontic ligature according to claim 18, further comprising a second protruding grip extension.

22. The elastic orthodontic ligature according to claim 18, wherein said grip extension protrudes out of a plane in which the ring member generally resides.

23. An elastic orthodontic ligature comprising: a ring member having a generally uniform first radial cross-sectional thickness; and at least a first grip extension protruding from said ring member; wherein the ligature has a second radial cross-sectional thickness at the grip extension which is greater than said first radial cross-sectional thickness, wherein said grip extension has a generally triangular configuration as viewed along a central axis of the ring member.

24. The elastic orthodontic ligature according to claim 23, wherein said second cross-sectional thickness is from about 2 to 2.5 times the first radial cross-sectional thickness.

25. The elastic orthodontic ligature according to claim 23, wherein said grip extension is adapted for grippable engagement with a tool.

26. The elastic orthodontic ligature according to claim 23, further comprising a second protruding grip extension.

27. The elastic orthodontic ligature according to claim 23, wherein said grip extension protrudes out of a plane in which the ring member generally resides.

* * * * *